US006363283B1

(12) United States Patent
Lyden

(10) Patent No.: US 6,363,283 B1
(45) Date of Patent: Mar. 26, 2002

(54) IMPLANTABLE CARDIAC STIMULATING DEVICE WITH OPTIMIZED DEMAND

(75) Inventor: Michael J. Lyden, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 09/693,396

(22) Filed: Oct. 20, 2000

Related U.S. Application Data

(62) Division of application No. 09/302,853, filed on Apr. 30, 1999.

(51) Int. Cl.[7] ................................................. A61N 1/36
(52) U.S. Cl. ....................................................... 607/34
(58) Field of Search ................................. 607/9, 11, 29, 607/34

(56) References Cited

U.S. PATENT DOCUMENTS

| | | | |
|---|---|---|---|
| 3,518,997 A | 7/1970 | Sessions | 128/422 |
| 4,031,899 A | 6/1977 | Renirie | 128/419 |
| 4,205,369 A | 5/1980 | Asano | 363/62 |
| 4,270,549 A | 6/1981 | Heilman | 128/784 |
| 4,291,707 A | 9/1981 | Heilman et al. | 128/784 |
| 4,316,472 A | 2/1982 | Mirowski et al. | 128/419 D |
| 4,321,928 A | 3/1982 | Elmqvist | 128/419 PG |
| 4,433,282 A | 2/1984 | Squires | 323/281 |
| 4,451,743 A | 5/1984 | Suzuki et al. | 307/110 |
| 4,488,555 A | 12/1984 | Imran | 128/419 PT |
| 4,567,900 A | 2/1986 | Moore | 128/784 |
| 4,606,350 A | 8/1986 | Frost | 128/419 PG |
| 4,860,769 A | 8/1989 | Fogarty et al. | 128/786 |
| 4,865,037 A | 9/1989 | Chin et al. | 128/419 D |
| 5,312,442 A | 5/1994 | O'Phelan | 607/5 |
| 5,385,575 A | 1/1995 | Adams | 607/5 |
| 5,387,228 A | 2/1995 | Shelton | 607/11 |
| 5,397,342 A | 3/1995 | Heil, et al. | 607/129 |
| 5,869,970 A | 2/1999 | Palm et al. | 324/433 |
| 5,876,423 A | 3/1999 | Braun | 607/29 |

FOREIGN PATENT DOCUMENTS

EP 0445800 9/1991 ............ A61N/1/39

OTHER PUBLICATIONS

DIckson, J.F., "On–chip high –voltage generation in MNOS Ics using an improved voltage multiplier technique", *IEEE Journal of Solid–State Circuits*, SC–11 (3), pp. 374–378, (Jun. 1976).

(List continued on next page.)

*Primary Examiner*—William E. Kamm
(74) *Attorney, Agent, or Firm*—Schwegman, Lundberg, Woessner & Kluth, P.A.

(57) ABSTRACT

It is important in cardiac pacing devices and systems to achieve efficient power utilization and conservation to extend the life of the battery cells, thereby extending the intervals between invasive medical procedures to replace components in the cardiac pacing system. A device and method are provided. The cardiac pacing device comprises a battery, a discrete time switched capacitor pacing power supply comprising a charge transfer capacitor bank comprising at least two capacitors, and a pace output supply capacitor which can discharge current to the tissue of a patient. A pacing supply design has a multiplicity of battery voltage multiplication factors and operating frequency settings. The pacing supply, voltage multiplier settings and operating frequency are automatically adjusted to compensate for changing pace output settings, load, cardiac cycle rate, and/or battery condition. The pacing supply voltage multiplier setting and frequency are varied over the useful life of the battery so that on average, from a beginning of life period for the battery to an end of life period for the battery, the voltage multiplier and the switching frequency increase. In the pacing device, the voltage multiplier and the switching frequency rate is determined by a reading of the rate of charging or charge time of a storage capacitor with the pacing device.

10 Claims, 2 Drawing Sheets

OTHER PUBLICATIONS

Gregorian, R., et al., *Analog MOS Integrated Circuits for Signal Processing*, John Wiley & Sons, pp. 463–464, (1986).

Harada, I., et al., "Characteristics analysis of Fibonacci-type SC transformer", *IEICE Transactions on Fundamentals of Electronics, Communications and Computer Sciences*, E75–A (6), pp. 655–662, (Jun. 1992).

Krummenacher, F., et al., "Higher sampling rates in SC circuits by on–chip clock voltage multiplication", *Proceedings of the European Solid State Circuits Conference*, pp. 123–126, (Sep. 1983).

Oto, D.H., et al., "High–voltage regulation and process considerations for high–density 5–V–only EEPROMs", *IEEE Journal of Solid–State Circuits*, SC–18 (5), pp. 532–538, (Oct. 1983).

Ryan, J.C., et al., "A four–chip implantable defibrillator/pacemaker chipset", *Proceedings of the IEEE Custom Integrated Circuits Conference*, San Diego, CA, pp. 7.6.1–7.6.4, (May 1989).

Singer, S., "Inductance–less up dc–dc converter", *IEEE Journal of Solid–State Circuits*, SC–17 (4), pp. 778–781, (Aug. 1982).

Tietze, U., et al., *Electronic Circuits : Design and Applications*, Chapter 18, Springer–Verlag, Berlin, pp. 477–524, (1991).

Ueno, F., et al., "Analysis and application of SC transforms by formulation", *Electronics and Communications in Japan*, Part 2, 73 (9), pp. 91–103, (1990).

Wayne, D., et al., "A single–chip hearing aid with 1V SC filters", *Proceedings of the IEEE Custom Integrated Circuits Conference*, pp. 7.5.1–7.5.4, (May 1992).

Witters, J.S., et al., "Analysis and modeling of on–chip high voltage generators circuits for use in EEPROM circuits", *IEEE Journal of Solid–State Circuits*, 24 (5), pp. 1372–1380, (Oct. 1989).

IMPLANTABLE CARDIAC STIMULATING DEVICE WITH OPTIMIZED DEMAND

CROSS REFERENCE TO RELATED APPLICATIONS

This application is a division of U.S. patent application Ser. No. 09/302,853, filed on Apr. 30, 1999, the specification of which is incorporated herein by reference.

FIELD OF THE INVENTION

This invention relates generally to an improved cardiac rhythm management apparatus, and more particularly to an implantable cardiac stimulating device incorporating means for leveling and/or optimizing the pulsatile pacing capacitor charging current demand from an internal battery power source.

BACKGROUND

Heart disease is a major cause of deaths in the United States and in other industrialized nations. One well-known treatment approach utilizes an implantable cardiac pacing device, through which relatively mild periodic electrical impulses are applied to epicardial or endocardial tissue as necessary to maintain normal sinus rhythm. More recently, cardioversion/defibrillation devices have been developed to counteract tachyarrhythmias (rapid disturbances in cardiac electrical activity). In particular, the conditions of ventricular tachycardia, ventricular flutter and ventricular fibrillation are widely believed to be the primary cause of sudden deaths associated with heart disease. Defibrillation devices also are utilized to counteract atrial tachyarrhythmic conditions, although such conditions are not considered life threatening unless they lead to a rapid ventricular disturbance or unless persistent enough to cause blood clots to form within the atrium because of pooling caused by poor atrial ejection.

Tachyarrhythmic conditions frequently can be corrected by applying relatively high energy electrical shocks to the heart, a technique often referred to as cardioversion. Cardioversion devices include implantable electronic standby defibrillators which, in response to the detection of an abnormally rapid cardiac rhythm, discharge sufficient energy through electrodes connected to the heart to depolarize and restore the heart to normal cardiac rhythm.

Cardioversion/defibrillation devices frequently include epicardially implanted electrodes. The surgical procedure required for implantation, i.e., thoracic surgery such as a median sternotomy or thoracotomy, is highly invasive and presents significant risks to the patient. It is highly desirable therefore to make every effort to reduce the number of times that invasive surgery is needed for a patient by having the life of each implanted device extended as long as possible. For this reason, extensive design and programming efforts are used to maximize the life of battery cells associated with cardiac pacing devices.

Electrodes implanted in the body for electrical cardioversion or defibrillation of the heart are well known. More specifically, electrodes implanted in or about the heart have been used to reverse (i.e., defibrillate or cardiovert) certain life-threatening cardiac arrhythmias, where electrical energy is applied to the heart via the electrodes to return the heart to normal sinus rhythm. See, for example, U.S. Pat. No. 4,291,707 to Heilman, relating to a planar patch defibrillation electrode.

The Heilman patent specifically discloses an implantable cardiac electrode comprised of a planar conductive material insulated completely on one side and partially on its other side. Apertures are provided around the insulated perimeter of the partially insulated side of the electrode to provide for efficient and uniform energy transfer to the heart tissue by eliminating the so called "edge-effect".

The amount of energy delivered by the electrodes to the heart during defibrillation (or cardioversion) depends on the placement of the electrodes and the ability of the electrodes to distribute the energy uniformly throughout a major portion of the heart. This energy is called the defibrillation or cardioversion energy.

U.S. Pat. No. 5,312,442 relates to the art of implantable cardiac defibrillators, and in particular, is related to an energy dissipation resistor capable of efficiently and reliably dissipating energy stored in the capacitor(s) of an implantable cardiac defibrillator. It is often the desire to dissipate electrical energy stored in defibrillator capacitors, rather than discharging to the heart, by diverting the capacitor voltage to an internal resistor. This is commonly referred to as an "internal dump". See, for example, U.S. Pat. Nos. 4,316,472 and 4,488,555 to Imran and Mirowski, respectively, where internal load resistors are shown. Presently, conventional resistive elements, such as carbon or ceramic resistors, and the like are used to dissipate the energy. Such conventional resistive elements tend to be large and bulky, and therefore difficult to package, often requiring extensive incoming inspection processes to assure that a desired reliability is achieved. In addition, although conventional resistive elements have proven generally effective in practice, worst case testing with multiple shock and internal dump episodes has resulted in heating of the resistive element and occasional destruction thereof.

For example, U.S. patent application Ser. No. 08/550,835, filed on Oct. 31, 1996, in the name of M. Brook and titled "Power Management System for an Implantable Device", shows a process for managing a power source, the power source having an output voltage, comprising the steps of:

periodically switching a load across the power source using a switch;

monitoring the output voltage of the power source using a dedicated voltage monitoring device and current monitoring device;

if the current monitoring device detects a current equal to or greater than a predetermined current threshold, opening the switch for one switching period; and if the output voltage is less than a selected threshold voltage, opening the switch until the output voltage is greater than the selected threshold voltage. This process is designed to and effectively does reduce the overall power utilization of a pacing system and can act to extend the life of a digitally charged power supply.

Cardiac pacing systems can tend to be quite active, with many different functions (sensing, pacing, charging, defibrillating, etc.) being provided by a single complex system. The activity of the system provides a significant drain on the usually single implanted battery which powers the entire system. Because the replacement of a battery is an invasive procedure which should be minimized in its frequency, anything which can be done to optimize the performance of an implanted pacing system or in anyway reduce the drain on the power supply to extend the life of the battery is a desirable goal.

Cardiac pacing systems are almost exclusively electronic, with no moving parts, so energy usage is already at relatively efficient rates. Any savings in energy usage is therefore very significant in extending the life of the battery in the pacing unit and in avoiding any invasive medical procedures. There are three general areas in which power utilization may be controlled: a) assuring that no work in performed when the inherent performance of the heart occurs, b) optimization of the function and power utilization of the components themselves, and c) programming of the pacing device to control the output of energy. Any new variation within these areas or new procedures which can be executed to reduce energy usage and prolong the life of the battery are highly desirable, in addition to the specific means shown in U.S. patent application Ser. No. 08/550,835 shown above.

Those skilled in the art will appreciate that the body has several mechanisms designed to adjust to metabolic demand by modifying cardiac output and, ultimately, oxygenation of tissue. The cardiac output may be increased or decreased by adjustment in sinus rate or stroke volume. Recognizing this fact, it has been possible to monitor metabolic demand by monitoring the sinus rate, the stroke volume and/or other activities which indicate different levels of use required by the patient's system. Both the monitoring of the patient's system and the exercise of these variations in pacing frequency require additional energy utilization and energy drain on the battery cell, and system must be put into effect to allow for these functions to be provided without shortening the life of the standard batteries used within the field.

U.S. Pat. No. 5,397,342 relates to body implantable tissue stimulation electrodes, e.g., for cardiac pacing or cardioversion/defibrillation, and more particularly to the deployment and implantation of such electrodes.

Examples of epicardial defibrillation electrodes are found in U.S. Pat. No. 4,567,900 (Moore), U.S. Pat. No. 4,291,707 (Heilman et al.), and U.S. Pat. No. 4,860,769 (Fogarty et al.). A pair of differently biased (e.g., oppositely polarized) epicardial electrodes can be employed, as shown in Moore. Alternatively, the Heilman patent discloses an intravenously inserted endocardial electrode arrangement in combination with a patch electrode positioned near the left ventricular apex.

U.S. Pat. No. 4,270,549 (Heilman) describes a technique for inserting and placing defibrillation electrodes, involving intravenous insertion of an endocardial electrode in combination with a patch electrode inserted through a skin incision and through a tunnel created inside the thorax and outside the pleural cavity. Alternatively, U.S. Pat. No. 4,865,037 (Chin et al.) discloses a technique for inserting separate electrodes into the intrapericardial space through catheters. An incision is formed in the upper abdominal wall. Then, tissues between the incision and pericardium are separated, and an incision is then made in the pericardium. A cannula containing a defibrillation electrode is inserted through these incisions, to enable positioning of the electrode in the pericardium. A second cannula containing a second electrode is inserted on the opposite side of the heart, in the same manner.

A problem, particularly with patch electrodes, is the current density gradient, i.e., maximum current density regions at the patch periphery. Current density gradients reduce the efficacy of the electrode, in terms of the ratio of useful cardioversion/defibrillation energy as compared to required pulse generator output energy. Alternative energy conserving means are desirable to overcome or balance these types of inefficiencies in cardiac pacing devices.

With the criticality of extending the life of battery cells and in maintaining a potentially large number of functions within the pacing device, any modification which can measurably extend the life of the battery can be advantageous to a cardiac pacing system.

To minimize the size of an implantable pacing device, the power source is usually a single battery cell for a brady pacemaker, and one or perhaps two cells of different chemistry types for an implantable defibrillator. Different battery types may be used within the same implantable defibrillator, one optimized for low-power high energy density for powering the internal circuitry of the device, and a separate high-power battery to provide the infrequent high energy charging of the defibrillator high output voltage capacitors.

The open circuit output voltage of these battery power sources are typically very low (e.g. 2.0~3.5V) because the batteries are often composed of a single cell. Therefore, fundamental to cardiac pacing devices and defibrillator design is the need for step-up voltage power supply circuitry. Defibrillators require the battery voltage to be stepped up to 100's of volts to charge the defibrillator output capacitors. Even brady-cardia pacing can require pace pulse amplitudes larger than can be delivered from the battery, the maximum programmable output amplitudes varies according to manufacture but is typically between 4.5 to 7.0V, because occasionally these higher pace amplitudes are required to properly depolarize the heart depending upon pacing lead type, placement, and health of the patient's heart.

There are many known circuit topologies for generating step-up as well as step-down voltages, as indicated by the representative reference list below:

K. Asano, "Voltage Dropping Circuit", U.S. Pat. No. 4,205, 369, May 27, 1980.

J. F. Dickson, "On-chip high -voltage generation in MNOS Ics using an improved voltage multiplier technique", IEEE J. of Solid-State Circuits, vol. SC-11, pp. 374–378, June 1976.

R. Gregorian and G. C. Temes, "Analog MOS Ics", Wiley, 1986, pp 463–464.

I. Harada et al., "Characteristics analysis of Fibonacci-type SC transformer", IEICE Trans. Fundamentals, vol. E75-A, no. 6, June 1992, pp 655–662.

F. Krummenacher et al., "Higher sampling rates in SC circuits by on-chip clock voltage multiplication, Proc. ESSCIRC, pp. 123–6, September 1983.

D. H. Oto et al., "High-voltage regulation and process considerations for high-density 5V-only EEPROMs", IEEE J. of Solid-State Circuits, vol. SC-18, pp. 532–538, October 1983.

J. C. Ryan, K. C. Carroll and B. D. Pless, "A four-chip implantable defibrillator/pacemaker chipset," Proc. IEEE 1989 Custom IC Conf., pp. 7.6.1–7.6.4, May 1989.

S. Singer, "Inductance-less up dc-dc converter", IEEE J. of Solid-State Circuits, vol. SC-17, pp. 778–781, August 1982.

D. R. Squires, "Monolithic Voltage Divider", U.S. Pat. No. 4,433,282, Feb. 21, 1984.

F. Suzuki and S. Ichikawa, "DC-to-DC Voltage Converter", U.S. Pat. No. 4,451,743, May 29, 1984.

U. Tietze and Ch. Schenk, Electronic Circuits, Sringer-Verlog, Berlin, 1991.

F. Ueno, T. Inone and T. Umeno, "Analysis and application of SC transforms by formulation", Electronics and Comm. In Japan, Pt. 2, vol. 73, no. 9, 1990, pp. 91–103.

J. S. Witters et al., "Analysis and modeling of on-chip high voltage generators circuits for use in EEPROM circuits," IEEE J. of Solid-State Circuits, vol. 23, pp. 1372–1380, October 1989.

D. Wayne et al., "A single-chip hearing aid with IV SC filters", Proc. IEEE 1992 CICC, pp. 7.5.1–7.5.4, May 1992.

BRIEF DESCRIPTION OF THE INVENTION

Some switched power supply designs use both inductors and capacitor energy storage elements, while others utilize capacitor only. Inductorless approaches are commonly employed by brady pacemakers to recharge the pacing output capacitor. These are typically switched capacitor designs which utilize one or more charge transfer capacitors, a set of interconnecting switches and non-overlapping digital clock signals that are used to coordinates charge extracted from the battery on one timing phase (the fill phase) and then deposited on the pacing output supply capacitor on a separate timing phase (the dump phase). Depending upon on the number of charge transfer capacitors and the switching configuration provided by the design, a multiplicity of voltage multiplication can be achieved from the same circuit depending upon setting.

For a brady pacing supply application, voltage multiplication settings of (0.5x, 0.66x, 1.0x, 1.5x, 2.0x, 3.0x), can be achieved using just two charge transfer capacitors, the battery which provides the input charge to the supply, and the pace output capacitor which is charged in anticipation to the next pace output pulse to be delivered to the heart.

Continual semiconductor technology and circuit design improvements have reduced internal operating currents making pacing current supply design and control increasingly important to extend operating life, and reduce the size of the implanted device.

Optimal control of the voltage multiplier setting can have very significant effects on device longevity as the current transfer ratio, the ratio of the output charge delivered to the pace output supply to input charge taken from the battery of the switched-C pacing supply is the inverse of the voltage multiplication ratio. Stated another way, for every microcoulomb of charge delivered to the output pacing supply at a multiplier setting of Kx, Kx times that amount of charge is removed from the battery.

Lead technology improvements now make capture thresholds of about 1.0V typical possible. Lower capture threshold leads, combined with automatic cardiac depolarization confirmation and threshold measurement systems (i.e. Autocapture) within the Brady pacemaker allow capture to be maintained at very small "safety" margins, the excess voltage above the measured capture threshold. This allows the pace output setting to be set just slightly above the capture threshold of the lead.

In this situation, pace output current draw from the battery can be reduced dramatically, by using voltage multiplication factors less than 1.0x. For example, the terminal voltage of Lithium Iodine battery at beginning of life will be very close to 2.8V. Therefore battery current required for the pacing output supply can be reduced by half by including and using a 0.5x voltage multiplier setting rather than the 1.0x voltage multiplier setting in the pacing supply. In this setting the pacing supply can achieve an output voltage of up to 1.4V and will do so at half the battery charge as the 1.0x setting. Previous designs have managed the programming of the pacing system with fixed constants look-up tables which allow the determination of the appropriate voltage multiplier setting Kx, given the desired pace amplitude setting. Typically, the relationship between pace amplitude and multiplier setting in the table-look-up is constant throughout the pulse generator life, and is calculated considering worst case operating conditions. Under worst case conditions, the multiplier setting must be chosen higher to compensate for low battery terminal voltage at end-of-life, even if a higher efficient, lower multiplier setting may be sufficient to recharge the pacing output capacitor earlier in life when the battery voltage is higher.

This present invention achieves novel current reduction and maximizes battery life by having the implanted device continually monitor and select the minimum possible voltage multiplier settings and the frequency of the switched capacitor timing clock as a function of the pacing output capacitor charge time (or alternatively charging rate) and battery condition.

The present invention relates to a cardiac pacing device with a pulsatile pacing output. The nature of the pulsatile output allows the opportunity to restore the charge lost by the pace output capacitor gradually over time up to a maximum interval equal to the paced cardiac cycle interval.

A switched capacitor pacing supply is used to restore charge to the pacing output capacitor between output pace pulses. The Switched-Capacitor pacing supply is provided with a multiplicity of programmable voltage multiplier settings (e.g. 0.5x, 0.66x, 1.0x, 1.5x, 2.0x, 3.0x), and a multiplicity of programmable operating frequencies (e.g. f=1/(n*0.5 mS)=15.6 Hz, 31.25 Hz, 62.5 Hz, 125 Hz, 250 Hz, 500 Hz, 500 Hz, 1000 Hz, 2000 Hz, for n={128,64,32, 16,8,4,2,1}).

The cardiac device and the method of use minimizes battery charge consumption by selecting the minimum voltage multiplier setting, and the minimum switched capacitor pacing supply operating frequency consistent with restoring requisite charge to the pace output capacitor in time before the next cardiac pace output pulse.

A switched capacitor pacing supply Multiplier, and Clock Frequency Control Algorithm are used to set the operating frequency and multiplier frequency. First the pacing supply operating frequency is set to the maximum rate. The voltage multiplier setting, Kx, is set to the minimum setting that is greater than Vpace/Vstop; this is the multiplier setting required to recharge the pacing supply cap at end-of-life battery resistance and terminal voltage.

Decrease Kx, and measure the time it takes to recharge the pacing supply capacitor from a paced event or alternately the charging rate to verify that the pacing supply capacitor is recharged within the cardiac pacing cycle interval. Continue to decrease Kx until the charge time becomes greater than the cardiac cycle interval. Restore the Kx setting to that just prior to that test cycle for which charge time exceeds the cardiac cycle interval.

Once the minimum Kx setting is determined, reduce the pacing supply operating clock in order that charge is extracted from the battery at the minimum rate required to recharge the pacing supply fully by the next commanded output pace. The following benefits are achieved by using the minimum operating frequency, which minimizes peak recharge current:

Battery output voltage transients are minimized thereby reducing the battery decoupling capacitor value.

Battery energy loss across its internal output impedance is minimized. For example, consider the battery energy loss for a Lithium Iodine with battery output resistance of 1 Kohm in recharging the pace output capacitance 4.0 uC at battery output current of 450 uA (battery terminal voltage=2.35V stop limit) in 8.8 mS compared to providing the same 4.0 uC but at an average current of 4 uA over a 1 second cardiac cycle interval. The "quick" recharge will dissipate 1.78 uJ while the slow recharge will dissipate only 0.016 uJ. The fast recharge case accounts for about 5% of the total energy of the pacemaker per cardiac cycle assuming a typical total pacemaker operating of 13 uA, a battery voltage of 2.8V, 36 uJ per 1 second cardiac cycle.

Minimizing the operating frequency and transient peak current may also reduce the potential for Li-Iodine charge loss due to trapped charge associated with high operating currents. This is a phenomenon which is well documented and understood for Li-Iodine chemistry whereby significant amounts of charge won't be extracted from the cell if the DC operating current is too high. Under high operating current conditions charge is extracted from the cell so fast that some charge becomes trapped within the cell and thereby not all of the charge capacity is available. For example, while a Li-Iodine cell may provide all of its rated capacity at a DC current load of 20 uA, it may only be able to supply<=80% of its capacity at 400 uA DC load. The effects of transient load current on reducing charge availability will certainly be lessened by the presence and the low pass filtering effect of the battery decoupling capacitor but to the authors knowledge has not widely been studied or been determined by industry.

The next step in the algorithm may then be to reduce the pacing supply operating clock from maximum using consecutively smaller discrete frequency settings ( e.g. f=1/(n*0.5 mS)=2000 Hz, 1000 Hz, 500 Hz, 250 Hz, 125 Hz, 62.5 Hz, 31.25 Hz, 15.6 Hz, for n={1,2,4,8,16,32,64,128}) until the charge time measurement exceeds the cardiac cycle interval.

A further refinement of the pacing supply operating frequency control is identified within this patent which accounts for the exponential charging current that results when operating a switched-C pacing supply at a fixed frequency to charge the pace output storage capacitor. When a switched-C pacing supply is operated at a fixed frequency, f, its first order electrical behavior is that of a resistor of a value of R=1/Cf. The value C depends on the charge transfer capacitor value as well as the fill and dump phase switch configuration, while f is simply the frequency at which fill and dump cycles occur per second. Although the minimum fixed frequency, f, selection criteria as determined above will provide the minimum number of charge transfer cycles required to recharge the pacing supply output capacitor within the cardiac pace cycle, the charge removed from the battery on each charge transfer cycle exponentially diminishes along the sequence of consecutive cycles as the pace output capacitor is charged. The rate of pacing supply charge extracted from the battery can be "leveled" further by varying the time interval between individual charge transfer cycles so that their occurrence is the inverse of the exponentially decaying charge transferred on each of the cycles. This improvement to the invention requires a variable clock frequency, where frequency increases toward the end of the charging interval (cardiac cycle) inverse to exponentially diminishing charge transferred on each cycle. Frequency control could be accomplished in a number of ways. For example, the embedded microcontroller, or state machine, could:

Count the total number of fill-dump cycles N needed to recharge the pacing capacitor.

Determine the paced cardiac cycle interval, Tcyc.

Measure the amount of discharge of the pace storage capacitor following the pace, $\Delta V$Total.

Measure the increase in voltage added to the pacing supply output capacitor, $\Delta VI$, after each charge transfer cycle.

Load a presettable delay counter for the next charge transfer cycle interval (I), with the value $$Ti = Tcyc\ (\Delta V(I)/\Delta V\text{Total}).$$

This relationship modulates the delay between subsequent charge transfer events, to level and equalize the average rate of charge extraction from the battery throughout the time the pacing supply output capacitor is charged by ensuring that the rate of charge transfer for each individual transfer cycle is equal to requisite charging rate needed to recharge the output capacitor in time for the next cardiac cycle;

$$\Delta V(I)/T(I) = \Delta V\text{Total}/Tcyc.$$

Periodic assessment of the battery and charge time measurements is performed by the pulse generator's imbedded controller frequently enough to ensure that the pace output regulation is maintained as the battery depletes. In addition, the pacing supply voltage multiplier setting and operating frequency are reassessed whenever pace output parameters are modified such as commonly occurs during initial implant, and patient follow-up. Reassessment can be triggered during ambulatory PG operation by significant paced output and or lead impedance changes, predetermined battery output resistance and/or voltage monitor points, or occurrence of the pacing supply not fully charge the pace output supply before a commanded pace output. The invention gradually increases pacing supply operating frequency, and multiplier setting as the battery output impedance increases and/or output voltage decreases as the cell is discharged.

A cardiac pacing device is described which comprises a battery, a switched capacitor pacing power supply comprising of one or more internal charge transfer capacitors, and a pace storage capacitor an element which can discharge current to the tissue of a patient in a pulsatile manner. While the invention applies to a variety of switched pacing power supply designs, a specific example of a switched capacitor power supply suitable for use in an implantable Brady pacemaker is described to illustrate an how frequency control can be utilized to shape the battery current load.

This supply is capable of operating in both voltage attenuation and multiplier modes while transferring charge from the battery to the pace storage capacitor, depending upon a programmable capacitor charge transfer switch configuration setting. The specific charge transfer configurations can be selected from a number of well know circuit topologies.

During the filling phase, the at least two charge transfer capacitors (24, 26) and a combination of switches inside said capacitor bank are configured to charge the charge transfer capacitors from the battery. During an alternate output, or dump phase, the switch configuration is used to move charge from the transfer capacitors the pacing supply output pacing capacitor (28). This process continues until the pacing supply output capacitor is charged to the desired pace output voltage (Vset) as determined by the Vset voltage comparator (18). The operating frequency of the charge transfer capacitor switches is varied over the useful life of the battery in order to control impedance presented to the battery terminals so that the battery pacing load current is approximately the average pacing supply charge required to replenish the pace output capacitor divided by the cardiac cycle. Operating frequency is adjusted so that charge is slowly extracted from the battery at a relatively uniform rate over the entire cardiac cycle. Viewed another way, the operating frequency of the switched-C pacing is controlled so that the effective load impedance presented to the battery by the pacing supply is high at the beginning of the battery's life when the battery's output resistance is low. As the battery discharges over life and its output resistance increases the pacing supplies operating frequency is increased in order to compensate, lowering the pacing supply impedance presented to the battery so that output pacing capacitor may be charged in time for the next pace command while keeping the battery load current constant. In the pacing device, the switching frequency rate is determined by a reading of the rate of charging of a storage capacitor with said pacing device or alternately measuring the overall charge time of the pace output capacitor.

The switching frequency rate is preferably determined by measuring the charge time of the pace output storage capacitor. The pacing device, preferably in response to the reading of output capacitor charge time, increases the pacing supply operating frequency is increased as the length of time to charge said storage capacitor increases.

Processes of this invention also include a process for increasing the life of a battery in a cardiac pacing device comprising the steps of monitoring a feature within the cardiac pacing device which indicates the relative strength of the battery compared to beginning of life conditions, as said monitoring shows a decrease in said relative strength of the battery compared to beginning of life conditions, and then modifying the voltage multiplier setting which vary the filling and output phases of the charge transfer.

Another process for charging a storage capacitor in a cardiac pacing device and then discharging the storage capacitor to effect a pace comprises the steps of:

a. monitoring a feature within the cardiac pacing device which indicates the relative strength of a battery compared to a defined initial battery strength, b. as said monitoring shows a decrease in said relative strength of the battery compared to said initial strength battery strength, selecting an alternate voltage multiplier setting by modifying the charge transfer capacitor configuration during the filling and output phase in said cardiac pacing device which are used to store charge in a power supply for a storage capacitor at a frequency of switching, and c. increasing the frequency of switching at which the at least two charge transfer capacitors are alternatively reconfigured between filling and output phases.

DETAILED DESCRIPTION OF THE PRESENT INVENTION

Figure 1:
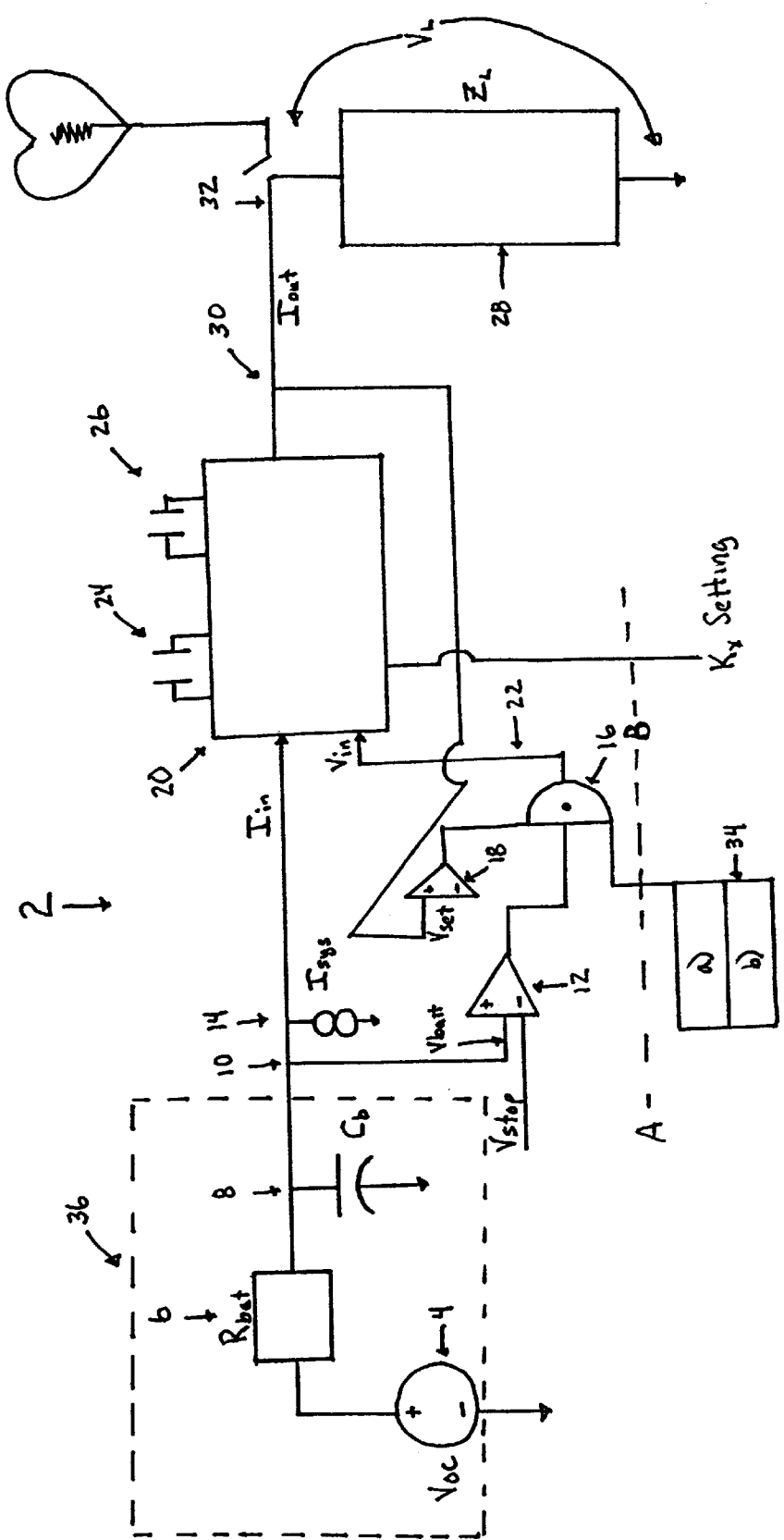
FIG. 1 shows a simplified circuit diagram of the system of the present invention.

The present invention describes a process and apparatus which provides a means for charging a pacemaker output capacitor for use in pacing devices where pulsed outputs must be supplied by the device. The charging circuit for the output capacitor uses a variable frequency capacitive charge pump. The variable frequency in the charge pump is particularly effective where the chemistry of the battery (e.g., a LiI battery or LiI-type battery) displays series impedance increases as energy is depleted from the battery cell. The process of the present invention converts a fixed battery voltage (e.g., such as the 2.8 V typical of a LiI battery) into a variable output voltage which is stored in an output capacitor. The output voltage may be programmed at whatever level is required by the pacing device, but for a Brady pacemaker is usually within the range of 0.5 to 7.0 Volts. The preferred circuit comprises at least two capacitors (e.g., banks of 2 to 10 or more capacitors may be used) and a combination of switches to accomplish the voltage conversion in the present invention. The capacitors and switches are configured within the pacing power supply so that the capacitors are alternatively configured in a filling configuration and an output "dump" configuration, to effect charge transfer from the battery to the pace output. For example, two charge transfer capacitors can be used to form a voltage doubler ( Kx=2.0). In such a design, the charge transfer capacitors are each connected in parallel across the battery output terminals during the filling phase and charged to battery potential ( e.g 2.8V). During the dump phase, the charge transfer capacitors are disconnected from the battery and connected in series with the output capacitor, under steady state conditions the pacing supply output capacitor is charged to 2x battery terminal voltage ( e.g. 5.6V ). There is preferably further control circuitry which is able to modify the filling and output phases of this charging process so that a multiplicity of voltage multiplier settings are attainable. The output capacitor charge voltage can be varied at any time from, for example, 0.5 to 5.0 volts. Switching of the configuration of the capacitors between the filling and output configurations is performed at controlled, relatively high frequency so that the output capacitor may still be charge at a rapid rate. Typically the rate of charging may be between 400 milliseconds (corresponding to 185 ppm) and 2 seconds (corresponding to 30 ppm) depending upon the desired pace output rate. One aspect of the present invention is that the switching frequency between the filling and output charge transfer configurations can be, and preferably is, varied over the useful life of the battery which is used to power the pacing device.

The cardiac pacing device may, for example, comprise:

a) a battery, b) a discrete time (i.e., its operation is not continuous, but episodic, or its operation is defined and/or authorized at discrete points of time), switched capacitor pacing power supply comprising an internal charge transfer capacitor bank comprising at least two capacitors, c) a pace output capacitor, and d) a switch that can discharge current to tissue of a patient.

The cardiac pacing device may be constructed whereby the switched capacitor pacing power supply has more than one programmable voltage multiplier settings, and more than one programmable operating frequency. The cardiac pacing device may also have the switched pacing power supply is connected to a memory controlling voltage multiplier settings and operating frequency so that said voltage multiplier settings and said operating frequency are varied automatically by the device over the useful life of the battery.

The functional operation of the variable frequency device and its benefits can be understood from the following description. The combination of a) switched transfer capacitor value and b) the switching frequency presents to the system an equivalent series resistance between the pacing device battery and the output capacitor. By varying the frequency, this equivalent series resistance will in turn vary as well. At the beginning of battery life (BOL), the battery cell impedance will be relatively low. Under this condition, the equivalent series resistance of the charge circuit should be selected to optimize both charge time and battery current drain for the BOL conditions. Specifically, this series convertor resistance should be low enough to provide an adequately short charge time consistent with the present pace pulse output rate of the pacemaker (e.g., 400 ms (185 ppm) to 2.0 second (30 ppm), but the series resistance should be high enough to preclude exaggeratedly fast charge times that would resulting in excessive peak battery currents. For example, at a pace output setting of 3.5V, 0.4 mS pulse width, 500 Ohm lead, a 10 uF output capacitor will be discharged to about 3.25V after the pace pulse is delivered. A switched capacitor supply operating at 2 Khz, using qty 2, 0.1 uF charge transfer capacitors, in a 1.5x multiplier setting will recharge the output capacitor from 3.2V to 3.5V in as few as qty 6 cycles, or about 3 mSecs, transferring approximately 4 uC within 3 mSec from the battery terminal resulting in a peak battery current during the recharge interval of 1.3 mA. If this latter event should happen, the too high current drain will cause fluctuations in battery cell voltage to occur. In an extreme case, battery voltage can fluctuate to levels that are low enough to cause a reset of the pacing device to be initiated depending upon the size of the battery decoupling capacitor. These battery voltage fluctuations could interfere with various device features such as sense amplifier performance, estimated replacement time (ERT) measurement, and other performance functions of the device. The process may therefore operate wherein the frequency of switching and/or a functional setting on a multiplier (after this self-applied analysis and comparison is made) effects a battery current profile that increases battery longevity from a standard frequency (e.g., a default or preprogrammed frequency) of switching and/or standard (e.g., a default or preprogrammed setting on the multiplier) functional setting on a multiplier.

Figure 2:
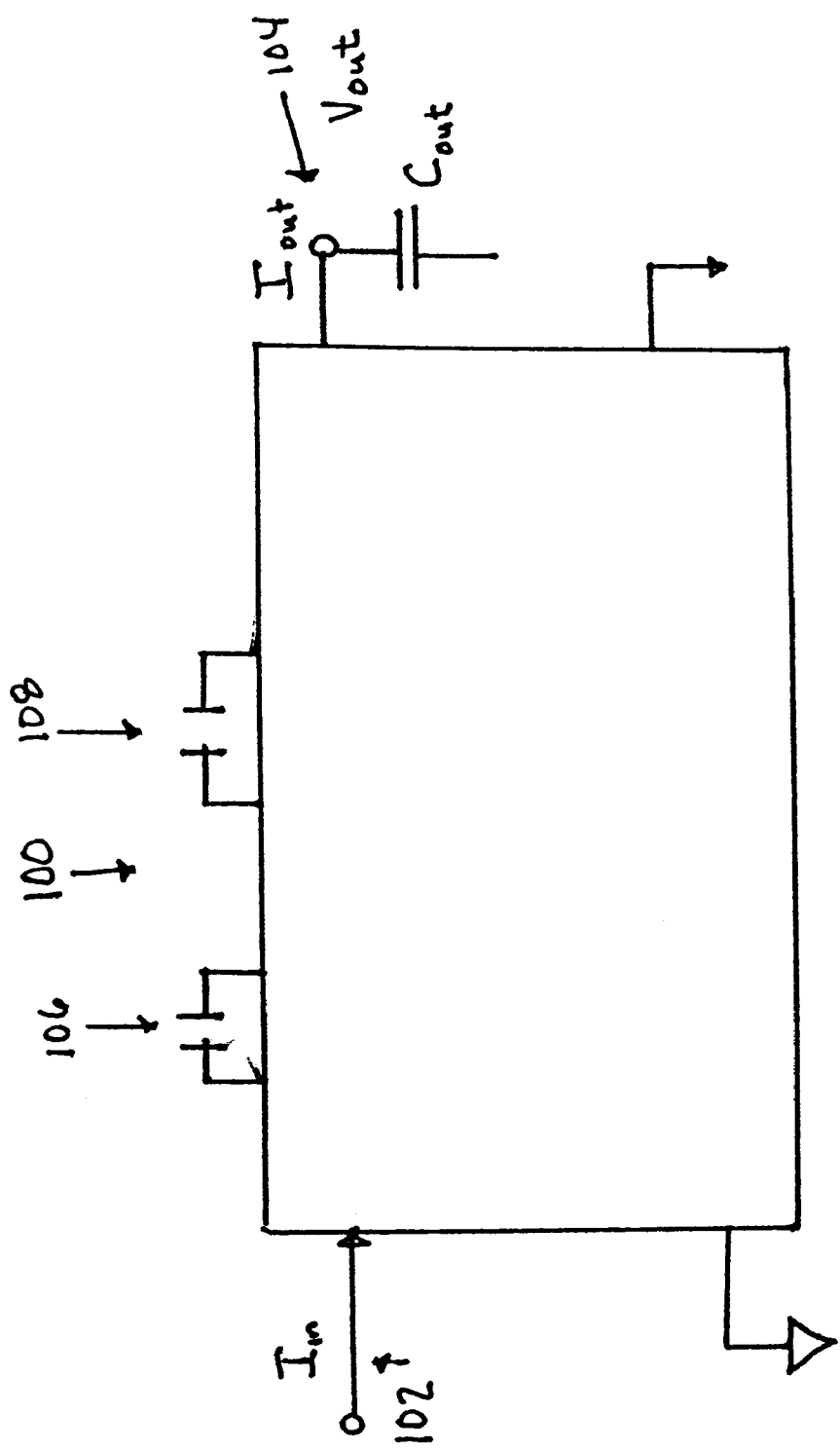
FIG. 2 shows the current and voltage relationship of the input and output terminals of the pacing supply.

As the LiI battery capacity is depleted over time, the series battery impedance increases. As a result, the optimal converter series resistance decreases correspondingly. The system of the present invention addresses this decrease in converter series resistance by increasing the converter frequency. As a result, the optimal capacitor charge time, as well as the optimal battery current drain may be maintained. The variation in converter frequency may be performed automatically by the pacemaker based upon parameters preset within the programming of the device such as the last measured time charge, an average of recent past time charges, and the like. This variation in the switching frequency of the charge circuit is at least one of the important differences over prior art pacemakers which fix a frequency over the life of the device. A fixed frequency will not be extended to the level capable in the practice of the present invention. As a practical matter the use of fixed voltage multiplier setting mapping to pace amplitude setting, also means that current drain for charging the output capacitors is relatively high at BOL to enable an adequately short charge time to be maintained at the End Of Life (EOL) period nearing depletion of the battery. If a fixed mapping between pace amplitude and voltage multiplier settings is used throughout life, a significant charge inefficiency applies to the top of the pace amplitude range defined for each multiplier setting because it will often be the case that a lower multiplier setting could be used at beginning through mid-life to achieve adequate charge times. FIG. 2 illustrates that battery charge comes at a significant cost at increasing higher pacing supply voltage multiplier settings.

Specifically, the present invention improves upon the efficiency and even the performance under extreme conditions of previous systems by altering the pacing supply voltage multiplier setting and switching frequency from relatively low frequencies at BOL to provide relatively high converter series resistance, to relatively high switching frequencies at EOL to provide relatively low converter switching resistance. This results in limiting the peak current drain at BOL, preventing fluctuations in voltage, while maintaining an adequately short charge time at EOL. This combination assists in increasing the effective life of the battery cell, and extends the period wherein invasive replacement of the battery cell must take place.

Charging System Overview

The system of FIG. 1 charges the load 28 capacitance using switching power supply 20 and battery 36. As shown in FIG. 1, battery 36 is modeled using idealized elements, such as ideal voltage supply 4, internal impedance 6 and internal capacitance 8. Internal impedance 6 varies primarily as a function battery charge depletion but can exhibit additional increases in apparent output impedance under the influence of the temporary increases in current drawn from battery 36 and the power drawn from battery 36. For example, internal impedance 6 may increase temporarily when large currents are demanded from battery 36. Internal impedance 6 also may increase as a function of power delivered by battery 36. An increase in internal impedance 6 results in a lowering of output voltage at node 10.

The battery output voltage at node 10, Vbatt will fall when charging the load 28 using switching power supply 20. In one embodiment, the system ensures that this drop in voltage does not fall below a Vstop voltage reference level due to charging of the load 28. For example, in FIG. 1, an input clock signal, CLK, to switching power supply 20 is used to activate or deactivate the switching power supply 20. Comparator 12 monitors the voltage at node 10, Vbatt, and compares it with the voltage reference Vstop to deactivate the switching power supply should the voltage at node 10 fall below Vstop. The deactivation is accomplished by a signal to logic "AND" gate 16. Other circuit configurations are possible without departing from the present invention. Vstop is generally selected to ensure that the battery voltage at node 10 does not fall below a predetermined safe operating voltage. This prevents the battery voltage from falling below the minimum required to properly operate the electronics in the system and prevents the system from entering a "reset" condition during charging cycles.

Another control feature found in the system of FIG. 2 is the Vset control, which inhibits charging of load 28 once the voltage across the pace output capacitor at node 30 has reached a desired value. In the circuit of FIG. 1, a voltage from node 30 is sampled and compared to a desired Vset voltage by comparator 18. Once the sampled voltage reaches the desired Vset voltage, a signal is sent to logic "AND" gate 16 to inhibit further charging of the load 28 by switching power supply 20. In one embodiment a voltage divider network is used between node 30 and comparator 18, since the voltages sampled may be large relative to the power supply used to power comparator 18. In the embodiment where a voltage divider is used, the Vset voltage may also be set using the known voltage divider ratio.

The clock controller or frequency controller 34 is used to control the frequency of the switched-capacitor pacing supply (e.g., 2 kHz/n). It is a programmable frequency divider which divides an input clock frequency, e.g. 2 Khz, by a presettable integer count, n, loaded by the internal pacemaker controller to produce the switched capacitor operating frequency=2 Khz/n. For example, the controller can command a multiplicity of switched capacitors pacing supply operating frequencies, f=1/(n*0.5 mS)=15.6 Hz, 31.25 Hz, 62.5 Hz, 125 Hz, 250 Hz, 500 Hz, 500 Hz, 1000 Hz, 2000 Hz, for n={128,64,32,16,8,4,2,1}. The internal pacemaker controller controls the pacing supply voltage multiplication setting through a digital control bus (37) to specify the multiplicity of possible settings ( e.g. 0.5x, 0.66x, 1.0x, 1.5x, 2.0x, 3.0x), the switched-capacitor pacing supply (20) takes this bus as an input and modifies the charge transfer capacitor (24, 26) filling and output phase switch topology in order to achieve the voltage multiplication specified.

A schematic of one type of pacing system 2 according to the present invention is shown in FIG. 1. The battery 4 and the battery resistance 6 lead past the battery capacitor 8 (Cb). At a junction 10 the electrical path divides into two paths. The first path leads to the battery voltage Vstop comparator 12 and the second path provides power to the internal circuitry represented in FIG. 1 simply as a current load 14. The second path continues on into the switched capacitor power supply 20, which is shown as having two charge transfer capacitors 24 26. The first path through the battery voltage Vstop comparator 12 leads is used to enable and disable switched capacitor 16. The pacing supply digital clock is enabled as long the battery voltage, Vbatt, remains above the Vstop limit and is applied to the power supply 20 along path 22. The charge from the battery 36, is transferred by the pacing power supply 20 passes through the charge transfer capacitors 24, 26 junction 30 through line 32 and is used to charge the pacing output capacitor 28. As noted, the portion of the pacing unit 2 above line A-B is a conventional design. In the practice of the present invention, a frequency controlling circuitry or digital clock divider 34 controls the operating clock frequency line 22, of the switched-capacitor power supply 20 through line 22. The frequency controlling circuitry 34 has the capability of having the frequency varied without invasion of any patient in whom the pacing system 2 has been implanted. Variation in the frequency may be effected by any convenient mechanism, particularly programs within the pacing device 2 in combination with a conventional clock divider circuit whereby a high frequency clock reference is digitally divided by n by employing a programmable counter. For example, the embedded pacemaker controller may use the frequency controlling circuitry 34 to effect a) gradually changes to the frequency over a time period in which the battery charge is expected to diminish under programmed usage, b) a timing function which gradually changes the frequency at specific time intervals after the pacing device 2 has been activated in a patient, or c) samples or reads the actual current/voltage/battery resistance and this information is used by a logic function (hardware, software, chip, switch, etc.) to alter the frequency of the current. It is preferred that the frequency be altered by a program within the device which does not need any outside monitoring or reprogramming, which would indicate a preference for the latter three types of systems.

FIG. 2 shows the current and voltage relationship of the input terminal 102 and output terminal 104 of the pacing supply 100. The voltage multiplication factor, kx, is based upon the electronic structure and number of switching capacitors 106, 108.

What is claimed:

1. A process for charging a storage capacitor in a cardiac pacing device and then discharging the storage capacitor to effect a pace, the process comprising:

monitoring a feature within the cardiac pacing device which indicates the relative strength of a battery compared to a defined initial battery strength;

as said monitoring shows a decrease in said relative strength of the battery compared to said initial strength battery strength, alternately configuring at least two capacitors in said cardiac pacing device which are used to transfer charge from the power supply to the storage capacitor at a frequency of switching; and increasing the frequency of switching at which the at least two charge transfer capacitors are alternatively configured in a charge filling phase from the battery and a charge delivery phase to a pace output capacitor.

2. The process of claim 1 wherein said monitoring is done by measuring a rate of charging for at least one capacitor in said cardiac pacing device.

3. The process of claim 1 wherein said frequency of switching and/or a functional setting on a multiplier effects a battery current profile that increases battery longevity from a standard frequency of switching and/or standard functional setting on a multiplier.

4. The process of claim 1 wherein each change in frequency is based upon a monitoring of a property or event in a previous pace or in a previous series of paces.

5. The process of claim 1 wherein:

a) the operating frequency is initially set to a maximum rate;

b) then the voltage multiplier setting, Kx, is set to the minimum setting that is greater than Vpace/Vstop;

c) Kx is then decreased, and time is measured for how long it takes to recharge the pacing supply capacitor from a paced event or the charging rate to verify that the pacing supply capacitor is recharged within the cardiac pacing cycle interval;

d) Kx is decreased until the charge time becomes greater than a cardiac cycle interval; and e) the Kx setting is restored to that just prior to a) for which charge time exceeds the cardiac cycle interval.

6. The process of claim 5 wherein once the minimum Kx setting is determined, the pacing supply operating clock is reduced so that charge is extracted from the battery at the minimum rate required to recharge pacing supply fully by a next commanded output pace.

7. A method for charging a storage capacitor in a cardiac pacing device and then discharging the storage capacitor to effect a pace, the process comprising:

a) during a filling phase, at least two charge transfer capacitors and a combination of switches inside said capacitor bank are configured to charge the charge transfer capacitors from the battery;

b) during a dump phase, the switch configuration is used to move charge from the transfer capacitors to a pacing supply output capacitor (28);

c) with a) and b) continuing until the pacing supply output capacitor is charged to a desired pace output voltage (Vset) as determined by a Vset voltage comparator;

d) the operating frequency of the charge transfer capacitor switches is varied over the useful life of the battery in order to control impedance presented to the battery terminals so that the battery pacing load current is approximately the average pacing supply charge required to replenish the pacing supply output capacitor divided by the cardiac cycle.

8. The method of claim 7 wherein operating frequency is adjusted so that charge is slowly extracted from the battery at a relatively uniform rate over the entire cardiac cycle.

9. The method of claim 8 wherein as the battery discharges over life and its output resistance increases, the pacing supply operating frequency is increased, lowering pacing supply impedance presented to the battery so that pacing supply output capacitor may be charged in time for the next pace command while keeping the battery load current constant.

10. A process for charging a storage capacitor in a cardiac pacing device and then discharging the storage capacitor to effect a pace, the process comprising:

monitoring a feature within the cardiac pacing device which indicates the relative strength of a battery compared to a defined initial battery strength, wherein said monitoring is done by measuring a rate of charging for at least one capacitor in said cardiac pacing device;

as said monitoring shows a decrease in said relative strength of the battery compared to said initial strength battery strength, alternately configuring at least two capacitors in said cardiac pacing device which are used to transfer charge from the power supply to the storage capacitor at a frequency of switching; and increasing the frequency of switching at which the at least two charge transfer capacitors are alternatively configured in a charge filling phase from the battery and a charge delivery phase to a pace output capacitor, wherein each change in frequency is based upon a monitoring of a property or event in a previous pace or in a previous series of paces.

* * * * *